US005538851A

United States Patent [19]

Fach et al.

[11] Patent Number: 5,538,851

[45] Date of Patent: Jul. 23, 1996

[54] **PRIMERS FOR THE AMPLIFICATION OF GENES CODING FOR THE ENTEROTOXIN AND THE LECITHINASE OF *CLOSTRIDIUM PERFRINGENS* AND THEIR APPLICATION TO THE DETERMINATION OF THE PRESENCE AND NUMERATION OF THESE BACTERIAE**

[75] Inventors: Patrick Fach, Creteil; Jean-Pierre Guillou, Chennevieres; Michel Popoff, Clamart, all of France

[73] Assignee: Institut Pasteur and Cneva, France

[21] Appl. No.: 172,026

[22] Filed: Dec. 22, 1993

[51] Int. Cl.[6] .............................. C12Q 1/68; C12P 19/34; C07H 21/04

[52] U.S. Cl. .......................... 435/6; 435/91.2; 536/24.32; 536/24.33

[58] Field of Search ................... 435/6, 91.2; 536/24.33, 536/24.32

[56] References Cited

FOREIGN PATENT DOCUMENTS

| | | |
|---|---|---|
| 409159A2 | 1/1991 | European Pat. Off. . |
| 03049699 | 4/1991 | Japan . |

OTHER PUBLICATIONS

Saito et al., *Int. J. Food Microbiol.* 17(1), 47–55 (1992).
Havard et al., *FEMS Microbiol. Lett.* 97, 77–82 (1992).
Saint-Joamis et al., *Mol. Gen. Genet.* 219, 453–460 (1989).
Czeczulin et al., *Infec. Immun.* 61(8), 3429–3439 (1993).
Fach et al., *J. Appl. Bacteriol.* 74, 61–68 (01 Jan. 1993).

*Primary Examiner*—W. Gary Jones
*Assistant Examiner*—Kenneth R. Horlick
*Attorney, Agent, or Firm*—Bierman and Muserlian

[57] ABSTRACT

Specific primers useful for the detection of the presence of lecithinase or enterotoxin genes or the presence of *Clostridium perfringens* bacteria in a sample by a polymerase chain reaction, particularly, in food sample or fecal samples.

4 Claims, 1 Drawing Sheet

PRIMERS FOR THE AMPLIFICATION OF GENES CODING FOR THE ENTEROTOXIN AND THE LECITHINASE OF *CLOSTRIDIUM PERFRINGENS* AND THEIR APPLICATION TO THE DETERMINATION OF THE PRESENCE AND NUMERATION OF THESE BACTERIAE

The present invention relates to primers for the amplification of genes coding for the enterotoxin and the lecithinase, also called phospholipase C, of *Clostridium perfringens*.

Another object of the invention is the application of these primers for the detection and the numeration of *C. perfringens*.

BACKGROUND OF THE INVENTION

*Clostridium perfringens* type A is widely distributed (soil, sewage, intestinal tracts of humans and animals . . . ), and is a common causative agent of bacterial food poisoning outbreaks worldwide. The symptoms, predominantly diarrhea and abdominal pain, appear 6 to 24 hours after ingestion of contaminated food. Vomiting and fever are unusual. Death occurs occasionally among debilitated persons, particularly the elderly.

*C. perfringens* enterotoxin CPE which is produced during the sporulation phase has been shown to produce the symptoms associated with *C. perfringens* food poisoning. The illness is caused by the ingestion of food that contains larger number of vegetative enterotoxigenic *C. perfringens* (more than $10^5$ organisms per g). These bacteriae multiply and sporulate, releasing CPE into the intestine.

A *C. perfringens* count of more than $10^6$/g in fecal samples of ill persons is indicative of *C. perfringens* food poisoning. In addition, CPE detection directly in fecal samples is a valuable method confirming the diagnosis.

The epidemiological investigations involve *C. perfringens* numeration in suspected foods. The characterization of the enterotoxigenic *C. perfringens* strains is not used routinely, since *C. perfringens* sporulates poorly in usual culture media.

Recently, CPE and phospholipase C gene sequences have been determined (VAN DAMME et al. 1989, Ant. Van Leeuwen 56, 181–190; TSO J. and SIEBEL, 1989. Infect. Immun. 57: 468–476, TITBALL et al. 1989 Infect. Immun. 57:367–376). The phospholipase C gene is located on a variable region of the chromosomal DNA in all *C. perfringens* toxinotypes whereas the distribution of CPE gene is restricted. Only 6% of the *C. perfringens* isolates from various origins showed the presence of CPE gene by DNA-DNA hybridization. This ratio is higher (59%) among *C. perfringens* strains isolated from confirmed outbreaks of food poisoning. In the standard methods, the enterotoxin detection by biological or immunological tests requires previously the sporulation of *C. perfringens*. Several specific medium and protocols for *C. perfringens* sporulation have been described, but they are time consuming and many *C. perfringens* strains do not sporulate or very poorly (DUCAN and STRONG, 1968. Appl. Microbiol. 16: 82; PHILIPS, 1986, Lett. Appl. Microbiol 3: 77–79), which impairs the CPE detection.

A method for the detection of *C. perfringens* by polymerase chain reaction (PCR) has been disclosed during the third Congress of the French Society of Microbiology (Apr. 21–24, 1992) through a poster of FACH et al.

The method consisted of amplification of the parts of the genes encoding the α-toxin, also called lecithinase, and the enterotoxin of *C. perfringens* by using oligonucleotidic primers which were choosen in these genes. However, the sequence of the primers used for carrying out this method was not disclosed and the sensitivity mentioned by the authors was low, i.e. from 500 to 5000 bacteriae per gram of feces.

Moreover, the results were obtained on feces artificially contaminated and not on feces from contaminated patients or no contaminated food.

SUMMARY OF THE INVENTION

The inventors have thus sought to elaborate a sensitive and reliable method allowing the detection of low quantities of bacteriae in samples of different origins, such as in feces or food, in a raw form.

They have surprisingly shown that it is necessary to choose the primers in some well determined regions of the genes, as well as in the gene of the enterotoxin and in the one of the lecithinase.

Besides, they have carried out a process for the treatment of foods samples, allowing a specific, sensitive and reliable determination of the presence of the *C. perfringens* contained in these foods.

The present invention first relates to primers for the amplification of the gene encoding the lecithinase of *C. perfringens*, also called alphatoxin or phospholipase C, corresponding to a part of the sequence of the gene comprised between the nucleotides 1350 and 1850, and preferentially between nucleotides 1350 and 1470 or 1650 and 1850, and which can amplify at least a part of the said gene, by cooperating with other primers having similar features and having a reversed polarity.

The said primers comprise preferentially from 10 to 40 and more preferentially from 10 to 30 nucleotides and their sequences can be one of the following ones:

SEQ ID1 (PL3) AAG TTA CCT TTG CTG CAT AAT CCC
SEQ ID2 (PL7) ATA GAT ACT CCA TAT CAT CCT GCT
SEQ ID3 (Plc) TCA AAA GAA TAT GCA AGA GGT
SEQ ID4 (PL1) TTCTAT CTT GGA GAGG CTATGCAC
SEQ ID5 (PL4) GCTACTAGTTCTTTTACATTCTTTCC.

The invention relates also to primers for the amplification of the gene encoding enterotoxin of *C. perfringens*, corresponding to a part of the sequence of the gene comprised between the nucleotides 450 and 950 and preferentially between the nucleotides 450 and 550, or the nucleotides 750 and 950 of said gene, and which can amplify at least a part of the said gene, by cooperating with other primers having similar features and having a reversed polarity.

The said primers comprised prefentially from 10 to 40 and more preferentially from 10 to 30 nucleotides and their sequences can be one of the following ones:

SEQ ID6 (P145) GAA AGA TCT GTA TCT ACA ACT GCT GGT CC
SEQ ID7 (P146) GCT GGC TAA GAT TCT ATA TTT TTG TCC AGT
SEQ ID8 (Ent A) GAA CGC CAA TCA TAT AAA TTT CCA GCT GGG

The present invention relates moreover to a process for the determination of the presence of the gene encoding the lecithinase, or of the gene encoding the enterotoxin, in a sample, comprising the following steps:

the DNA from the sample is isolated, parts of the genes encoding the lecithinase, or the enterotoxin, are amplified by polymerization chain reaction (PCR) with the help of specific primers, such as defined hereabove respectively for the lecithinase and for the enterotoxin, the amplification products are determined with the help of known methods.

Another object of the present invention is a process for the determination of the presence, and the numeration of *C. perfringens* in a sample, wherein:

the DNA from the said sample is isolated, parts of the genes encoding the lecithinase and the enterotoxin are amplified by polymerase chain reaction with the help of specific primers such as defined hereabove for respectively the lecithinase and the enterotoxin, the amplification products are determined with the help of known methods.

The amplification products obtained by the process described hereabove can in particular be determined by electrophoresis on an agarose gel, followed by a transfer of the eluted DNA on "Nylon" membranes and by an hybridation with a labelled probe specific for the amplified part of the gene.

Other methods known by the man skilled in the art can also be used, if such methods are sufficiently specific and sensitive.

Such methods are in particular described in "The molecular cloning: A Laboratory Manual; SANDERS et al., Cold Spring Harbor Editor", in which the man skilled in the art can refer for carrying out the processes according to the present invention.

The choice of the hereabove described primers did not obviously emerge from the gene sequences such as published. Indeed, the man skilled in the art well knows that the choice of primers for the amplification of a given DNA part is difficult and that one can be faced with numerous difficulties.

For example, primers can lack specificity or be weakly thermodynamicly stable.

The man skilled in the art can also be faced with other technical difficulties from different types. Thus, the choice that has to be made by the man skilled in the art in the sequence of the gene is difficult because of the important number of possible combinations between the two primers corresponding respectively to sequences of the two strands, from the DNA molecule which has to be amplified.

The use of software helps the man skilled in the art in his choice but does not constitue a method leading automatically and obviously to primers permitting the sought amplification.

The primers such as defined hereabove are able to amplify the said genes if they cooperate with another primer having similar features but of reversed polarity. Indeed, the other primer must be situated on the strand of reversed polarity, called non-sense strand, in such a way that the polymerization of the two strands, initiated from the two primers produce two types of single strand DNA fragments which hybridate and form a double strand DNA molecule, called amplification product, which will be determined by known methods. The primer cooperating in the amplification of the fragment of the said gene has some similar features, i.e. that it is situated in the region of the said gene but on the strand of reversed polarity.

Preferentially, the combinations of the primers can be the following: PL1 and PL4, PL3 and PL7, P145 and P146, P145 and Ent A.

The processes hereabove described allow the detection of *C. perfringens* in a lot of samples, such as feces or food products, such as convenience foods, without necessiting a pretreatment of the sample.

In a general way, heating of the samples at temperature lysing the bacteriae and separating by centrifugation the DNA from bacterial fragments is sufficient.

In the case of food samples, in particular meats, it can be necessary to perform a pretreatment of the sample in order to eliminate substances which can interference with the polymerase chain reaction.

Thus, the DNA can be isolated from a food sample by a process comprising the following steps:

the sample is incubated in a medium allowing the growth of *C. perfringers,* the bacteriae are separated from the food particles by centrifugation, the bacteriae are put in contact with a resin which lyses them, the DNA is separated from bacterial fragments.

MATERIALS AND METHODS

Bacterial Strains

Figure 1A:
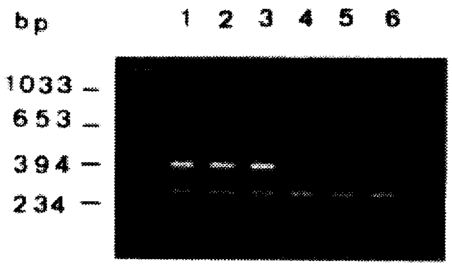
FIG. 1A is an ethidium bromide stained agarose gel of amplification products obtained with enterotoxigenic *C. perfringens* type A strain 8-6 (1), type D strain IP76 (2), type E strain NCIB10748 (3), and non enterotoxigenic *C. perfringens* type A strain ATCC13124 (4), type B strain CN3922 (5) and type C strain CWC236 (6).

All bacterial strains used in this study are listed in table 1. The others *C. perfringens* strains were isolated from food poisoning outbreaks and feces of children suffering from diarrhoea (see table 1).

Clostridium were grown, under anaerobic conditions, in TYG medium: trypticase (30 g/l), yeast extract (20 g/l), glucose (5 g/l) and cysteine HCl (0.5 g/l), pH 7,2. Strains were confirmed as *C. perfringens* by lactose fermentation, nitrate reduction, gelatinase production and absence of motility.

Standard Bacteriological Methods

For bacteriological food and feces analysis, 10 g of the samples were placed aseptically into sterile stomacher bags and homogenized for 2 minutes with 90 ml of peptoned water. One ml of decimal dilutions of the suspension was mixed with 9 ml SPS agar: Tryptone (15 g/l), yeast extract (10 g/l), feric citrate (0.5 g/l), sodium sulfite (0.5 g/l), sodium thioglycolate (0.1 g/l), tween 80 (0.005 g/l), polymyxine B sulfate (0.001 g/l), disodic sulfadiazine (0.12 g/l) and agar (14 g/l pH 7). After a 18 h anaerobic incubation at 46° C. the number of sulfito-reductor Clostridium was determined. Colonies surrounded with the black characteristic precipitate were identified by biochemical test (lactose fermentation, nitrate reduction, gelatinase production and motility).

Anti *C. perfringens* Enterotoxin Immunoglobulins

*C. perfringens* enterotoxin was purified from *C. perfringens* strain 8-6 and rabbit anti *C. perfringens* enterotoxin antibodies were prepared as previously described (POPOFF, 1984, FEMS MICROBIOL Let. 21: 1–5). Anti *C. perfringens* enterotoxin immunoglobulins were purified by immunoaffinity. *C. perfringens* enterotoxin (3–5 mg) was coupled to 1 g of cyanogen bromide—activated Sepharose 4B (Pharmacia, Paris, France) according to the instructions of the manufacturer. Five ml of rabbit anti *C. perfringens* enterotoxin serum were passed over the immuno affinity column. The column was washed with phosphate-buffered saline (PBS) until no protein was detected, and eluted with 1M acetic acid. Fractions of 200 μl were collected into tubes containing 100 μl TRIS 3M pH 8. The fractions containing anti *C. perfringens* enterotoxin immunoglobulins were dialyzed against PBS.

Preparation of Latex Beads

Coating of latex beads (Bacto Latex 0.81, Difco, USA) was performed as described (SHAHRABADI et al. 1984, Clin. Microbiol. 20: 339–341). Latex suspension (2–5 ml) was diluted in 15 ml of glycine buffer (0.1M glycine, 0.15M NaCl, pH 8.2) containing 200 μg of specific anti *C. perfringens* enterotoxin immunoglobulins, and homogenized for 1 minute at room temperature. Then, 1 volume of PBS—0.1% bovine serum albumine (BSA) was added. The mixture was shaken by vortex mixing, and stored at 4° C. The negative latex control was prepared as the same, but using non immune IgG (Sigma, Paris, France).

Slide Latex Agglutination Test (SLAT) for *C. perfringens* Enterotoxin Detection SLAT was performed on a glass slide by mixing 25 μl of coated latex and 25 μl of serial ten fold dilutions of samples in PBS—0,5% BSA.

The mixture was gently rotated and the results were recorded after 3 minutes.

The enterotoxin detection in *C. perfringens* strains was carried out using SLAT and culture supernatant from cultures in the Duncan and Strong sporulation medium (DAMME-JONGSTEN et al. J. Clin. Microbiol. 28: 131–133).

Fecal specimens were diluted at 1:10 in PBS—0.5% BSA, homogenized by vortexing, and centrifuged at 15 000×g for 30 minutes. The clarified supernatant was tested by SLAT.

Primers used in Duplex PCR

The oligonucleotides for PCR amplification and for hybridization used in this study, the primers PL3, PL7, PL1, PL4 and Plc were derived from the *C. perfringens* alphatoxin gene, the primers P145 and P146 and the probe Ent A were from the enterotoxin gene (VAN DAMME et al. 1989).

All the oligonucleotides were chemically synthesized by using a nucleic acid synthesizer (model 380 B; Applied Biosystems Inc. Foster City, Calif.).

Duplex PCR with Broth Culture

One ml of overnight bacterial cultures were transfered to a microcentrifuge tube and centrifuged at 12.000×g for 3 minutes. The pellet was resuspended in 100 μl water, heated at 100° C. for 10 minutes, and centrifugated at 12000×g for 10 minutes. Five μl of the supernatant were submitted to PCR using a PTC-100 programmable Thermal Controller (M.J. Research Inc. Watertown, Mass., USA). Each reaction tube contained 50 μl of a solution of 10 mM Tris-HCl pH 8.3, 50 mM KCl, 1.5 mM $MgCl_2$, 0.1 mg/ml gelatine, 200 μM of each of the deoxynucleotide (Boehringer Mannheim, Germany), 0.5 μM of each primer and DNA sample. Evaporation within the tube was prevented by the addition of 100 μl mineral oil (Sigma, SL-Lous, Mo., USA). The reaction mixtures were treated to 94° C. for 5 minutes to denature the DNA and then 2.5 units of Taq polymerase (Boehringer) were added to each tube. All PCR reaction were performed using 45 cycles of the optimized thermal profile: 30 s denaturation at 94° C., 30 s primer-annealing at 55° C. and 30 s primer-extension at 72° C. After the 45th cycle, the extension reaction was continued for another 10 minutes at 72° C., to ensure that the final extension steps were complete. Negative controls containing all reagents except template DNA were performed in each amplification set. To avoid contamination, sample preparation, PCR amplification and electrophoresis were performed in three different rooms.

Duplex PCR with Stool Samples

Stool samples (0,1 g) were weighed aseptically into sterile tubes and homogenized with 0,9 ml of water. Samples were centrifugated at 12.000×g for 3 minutes. The pellet was resuspended in 100 μl water, heated at 100° C. for 10 minutes, centrifugated at 12000×g for 10 minutes, and 5 μl of the supernatant were PCR amplified as described above.

Pretreatment of Food Samples before the Amplification Reaction a) Incubation of the sample.

The detection of viable bacteriae is of great importance in the food processes.

The discrimination between dead and live bacteriae can be performed by cultivating the sample.

For the detection of *C. perfringens*, 25 g of the sample are incubated in 225 ml of buffered peptonized water for 18 hours at 37° C. in anaerobiosis and without shaking.

The spores of *C. perfringens* are selected with the help of a thermal shock at 80° C. of the food culture before incubating.

b) Treatment of the sample for the PCR analysis.

After incubation of the food cultures, the food fragments are sedimentated and 1 ml of the enrichment medium is taken at the surface.

A low speed centrifugation (600 rpm) allows the elimination of the lowest food particles. The supernatent is recovered and centrifugated at a high speed (12 000 rpm) for 2 minutes. The supernatant is eliminated and the bacterial pellet is suspended in 2 ml of sterile water. The tube is then centrifuged at 12 000 rpm and the supernatant is eliminated with the help of a Pasteur pipette.

200 μl of the "InstaGene" matrix (commercialized by Biorad) are added on the pellet and incubated at 56° C. for 30 minutes. The tube is vortexed for 10 seconds and put in a water bath at 100° C. during 8 minutes. The tube is then vortexed for 10 seconds and centrifuged at 12 000 rpm for 3 minutes. 3 μl of the supernatant are taken in order to perform the duplex PCR which is finally performed on a volume of 50 μl.

Starting from 25 g of foods containing 10 or more than 10 *C. perfringens* allows the determination in the 15 μl of the amplified solution of the amplification product.

Gel Electrophoresis

A 10 μl aliquot of amplified DNA was examined after electrophoresis through a composite agarose gel consisting of 3% NuSieve agarose and 1% SeaKem agarose (FMC BioProducts, Ropckland, (Me., USA) and containing 0.5 μg/ml ethidium bromide, in 1×Tris-borate-EDTA buffer (0.089M Tris, 0.089M bioric acid, 0.002M EDTA, pH 8). Electrophoresis was carried out for 1 hour a t 80 V. The gel was examined visually with an ultra-violet transilluminator.

Hybridization Procedure

DNAs electrophoresed on agarose gel were transferred to "Nylon" membranes (Boehringer, Paris, France) using 0.4N NaOH and fixed by heating the membranes for 15 minutes at 120° C. Filters were pre-hybridized in 5×Saline Sodium Citrate buffer (SSC), 0.1% N-laurylsarcosine, 0.02% Sodium Dodecyl Sulfate (SDS) in 1% blocking reagent (Boehringer) at 65° C. for 1 hour. Hybridization occurred with Ent A or Plc oligonucleotide 3'-endlabelled by digoxigenin 11-DUTP with terminal deoxynucleotidyl-transferase (Boehringer). The probe was added to 50 ng/ml in the pre-hybridization solution and filters were incubated at 40° C. for 1 hour. After 2×SSC, 0.1% SDS washing, membranes were washed to a final stringency of 50° C. in 0.1×SSC, 0.1% SDS and detection was performed with alkaline phosphatase-labelled anti-digoxigenin antibody (Boehringer), nitroblue tetrayolium (NBT) and bromo-4-chloro-3-indolyl phosphate (BCIP) according to the instruction of the manufacturer (Boehringer).

EXAMPLE 1

Figure 1B:
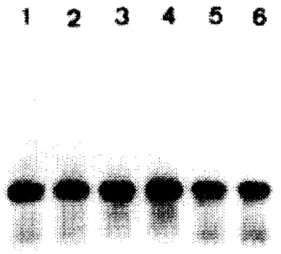
(FIG. 1B), and Southern hybridization with Plc (FIG. 1C), and EntA (Panel C) probes.
Figure 1C:
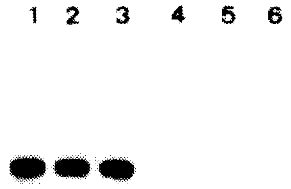

*C. perfringens* Duplex PCR Specificity and Characterization of the Enterotoxigenic Strains The specificity of the duplex PCR with the two primers sets derived from the phospholipase C and CPE genes was assessed by using different Clostridium species and various bacterial species frequently encountered in foods (table 1). The 283 bp amplification product was observed in ethidium bromide stained agarose gel with all *C. perfringens* strains tested (table 1). This amplification product had the expected size of the phospholipase C gene DNA fragment generated by PL3 and PL7 primers set. This result was confirmed by DNA-DNA hybridation with the internal primer Plc (FIG. 1).

The other bacterial strains tested showed no amplification products with the two primers sets PL3–PL7 and P145–P146 (table 1).

Seven *C. perfringens* strains out of 24 showed an additional 426 bp amplification product which corresponded to the expected size of the CPE DNA fragment delimited with P145 and P146. This 426 bp amplification product hybridized with the Ent A primer localized between P145 and P146 on the CPE DNA sequence and not with Plc primer derived from the phospholipase C gene (FIG. 1).

The *C. perfringens* strain 8.6 was found enterotoxinogenic by the duplex PCR amplification (table 1). This data is in agreement with the fact that this strain produced CPE using Vero cell cytotoxicity, mouse lethality and immunoprecipitation.

EXAMPLE 2

Sensitivity of the Duplex PCR using Broth Cultures

The duplex PCR was performed directly with broth cultures of the enterotoxogenic *C. perfringens* strain 8.6, in order to determine the sensitivity of the method. The number of bacteriae in culture samples was determined microscopically using a Petrov Chamber. The PCR amplification was carried out as described in material and methods. It was found that as few as 50 bacteria in the reaction volume yielded positive results after agarose gel electrophoresis and ethidium bromide staining. The sensitivity was 10 fold increased when the amplification products electrophoresed on agarose gel were transferred to nylon membrane and hybridized with digoxigenin labelled internal probes Ent A and Plc. In these condituions, the detection limit was approximately 5 bacteria in the reaction volume of the duplex PCR.

EXAMPLE 3

Application of the Duplex PCR to Stool Samples

Twenty three stool samples originated from a suspected *C. perfringens* food borne intoxication outbreak were investigated directly by the duplex PCR and standard microbiological methods for *C. perfringens* detection. Eighteen samples were found positive in the duplex PCR (table 2). All these samples yielded two amplifications products which has the expected size of the DNA fragments delimited by PL3–PL7 and P145–P146, and hybridized with the internal primers Plc and Ent A respectively, signifying that they contained enterotoxigenic *C. perfringens*. The sulfito reductor bacteria counted by the standard bacteriological methods ranged from less than $10^4$ to $10^8$ bacteria per gram. Five feces samples were found negative in the duplex PCR and DNA-DNA hybridization test. The corresponding sulfito-reductor bacteria counting was less than $10^4$ per gram for 3 samples, and $10^5$ to $2.10^5$ for the two other (table 2).

EXAMPLE 4

*C. perfringens* Enterotoxin SLAT in Stool Samples

The CPE was detected in 18 stool samples out of 23 by SLAT as described in material and methods (table 2). Enterotoxigenic *C. perfringens* was identified by the duplex PCR in 17 of these 18 SLAT positive stool samples. Four samples were negative with both tests.

One stool sample was shown to contain enterotoxigenic *C. perfringens* by the duplex PCR and no CPE by SLAT. The low number of enterotoxigenic *C. perfringens* (less than $10^4$ per gram) explained the absence of CPE in this example.

CPE was detected by SLAT in one stool sample (table 2) which was negative in the duplex PCR. The level of sulfito reductor bacteria in this sample was $10^5$ per gram. However, twenty *C. perfringens* clones isolated on sheep blood agar, were identified as enterotoxigenic *C. perfringens* by the duplex PCR.

EXAMPLE 5

Application of the Duplex PCR to Naturally and Artificially Contaminated Food Samples The food sample which was responsible for the food intoxication outbreak was found to contain enterotoxigenic *C. perfringens* by the duplex PCR performed directly without enrichment culture. The counting of sulfitoreductor bacteria was $10^5$ per g, and no CPE was detected by SLAT.

In order to investigate the sensitivity of this method, the duplex PCR was assayed directly with artificially contaminated food samples. The detection limit was found to be $10^5$ *C. perfringens* per g. The sensitivity was improved by using an overnight enrichment culture as described in material and methods. Among 59 naturally contaminated food samples, 2 were found to contain $5.10^5$ and $10^3$ *C. perfringens* per g respectively by the classical method and were positive by the duplex PCR.

All the 57 food samples which did not contain sulfitoreductor bacteria and were artificially contaminated (10 *C. perfringens* per g) gave a positive result in duplex PCR after enrichment culture (table 3).

CONCLUSION

All the 24 *C. perfringens* strains tested yielded the 426 bp DNA fragment hybridizing with the probe Plc, which corresponds to the presence of the phospholipase C gene. Seven of these *C. perfringens* strains (2 type A reference strains, 3 type A strains isolated from food, and 2 type D strains) showed an additional amplification product hybridizing with Ent A probe, which indicates the presence of the CPE gene.

The duplex PCR is specific of *C. perfringens*. No amplification product was observed with 27 Clostridium strains different from *C. perfringens* and 20 other bacteria species frequently encounted in foods.

An important advantage of this method is to identify easily and quickly the enterotoxigenic *C. perfringens* strains.

The duplex PCR can be used with *C. perfringens* grown in regular culture medium for anaerobic bacteria without DNA purification. The sensitivity of the duplex PCR using pure culture is 50 bacteria by visualization of ethidium bromide stained amplification product in agarose gel, and 5 bacteria in the reaction volume by DNA-DNA hybridization with the internal probes.

This duplex PCR DNA-DNA hybridization assay was tested with biological and food samples. Enterotoxigenic *C. perfringens* were detected directly in 18 among 23 stools samples from patients suffering food borne intoxication. These results were in agreement with the numeration of the sulfito reductor bacteria by the standard method and the detection of the CPE by SLAT, except for two stools samples. One stool sample containing $10^5$ sulfito reductor bacteria per gram and CPE by SLAT was found negative by the duplex PCR. But, individual *C. perfringens* clones isolated from this stool sample were identified as enterotoxigenic *C. perfringens* by the duplex PCR. The presence of PCR inhibitors in this sample accounts probably for this negative result. The other stool sample showed a low number of sulfito-reductor bacteria and no detectable CPE, but was positive in the duplex PCR. A contamination of this sample could explain the positive result in duplex PCR.

The detection limit of enterotoxigenic *C. perfringens* in stools by the duplex PCR is $10^4$ and $10^5$ per gram. This sensitivity is suitable for the diagnosis of *C. perfringens* food borne intoxication, since it has been reported that *C. perfringens* is recovered at high number ($10^6$ and more per g) in stools from patients suffering *C. perfringens* food borne intoxication.

Controls of food *C. perfringens* contamination constitute an important step in the prevention of food borne intoxication by this microorganism. The standard method routinely used detects sulfito-reductor bacteria which encompasse *C. perfringens* and also other Clostridium. The duplex PCR is specific of *C. perfringens* and discriminates the enterotoxigenic strains which are the causative agents of *C. perfringens* food borne intoxication. The sensitivity of this method (10 *C. perfringens* per g) performed with enrichment cultures of food samples is compatible with the prescribed detection levels for food controls. The limit of the duplex PCR directly with food samples without enrichment cultures is $10^5$ bacteria per g, the duplex PCR can be used directly when a *C. perfringens* food borne intoxication is suspected.

The duplex PCR is more rapid and simple than the standard procedure which needs additional bacteriological tests for the identification of the suspected clones. This method can be applied to food controls for the detection of *C. perfringens* and identification of the enterotoxigenic strains.

TABLE 1

Ability of duplex PCR to distinguish enterotoxigenic *C. perfringens* and *C. perfringens* between other Clostridium and other enterobacteria.

| Bacteria | Strain | PCR Result (1) |
|---|---|---|
| Clostridium perfringens type A | ATCC 13124 | + |
| Clostridium perfringens type B | CN 39.22 | + |
| Clostridium perfringens type C | CWC 236 | + |
| Clostridium perfringens type D | 2534 | + |
| Clostridium perfringens type D | 250 | + |
| Clostridium perfringens type D | A0 | + |
| Clostridium perfringens type D | 48 | + |
| Clostridium perfringens type D | 76 | ++ |
| Clostridium perfringens type D | 64/1 | ++ |
| Clostridium perfringens type E | NCIB 10748 | ++ |
| Clostridium perfringens | S-6 | ++ |
| Clostridium perfringens | 1088.0 | ++ |
| Clostridium perfringens | 4012 | ++ |
| Clostridium perfringens | 4086 | ++ |
| Clostridium perfringens | 4009 | + |
| Clostridium perfringens | 4010 | + |
| Clostridium perfringens | 4011 | + |
| Clostridium perfringens | 1089.1 | + |
| Clostridium perfringens | 1089.2 | + |
| Clostridium perfringens | 1089.3 | + |
| Clostridium perfringens | 1089.4 | + |
| Clostridium perfringens | 1089.5 | + |
| Clostridium perfringens | 1122 | + |
| Clostridium perfringens | 1513 | + |
| Clostridium spiraformé | 247 | − |
| Clostridium subterminale | ATCC 25774 | − |
| Clostridium septicum | ATCC 12464 | − |
| Clostridium limosum | 384 | − |

TABLE 1-continued

Ability of duplex PCR to distinguish enterotoxigenic *C. perfringens* and *C. perfringens* between other Clostridium and other enterobacteria.

| Bacteria | Strain | PCR Result (1) |
|---|---|---|
| *Clostridium beijerinckii* | VPI 5481 | – |
| *Clostridium mangenotii* | ATCC 25761 | – |
| *Clostridium chauvei* | IP 91 | – |
| *Bacillus thuringiensis* | 14001 | – |
| *Bacillus subtillis* | 168 | – |
| *Bacillus cereus* | LCHA 1203 | – |
| *Listeria monocytogenes* 1/2 a | A3 | – |
| *Listeria monocytogenes* 1/2 b | 13 | – |
| *Listeria monocytogenes* 4 b | 03 | – |
| *Listeria innocua* 6 a | C3 | – |
| *Listeria welshimeri* 6 b | E3 | – |
| *Listeria seeligeri* 1/2 b | D3 | – |
| *Clostridium botulinum* type A | ATCC 25763 | – |
| *Clostridium botulinum* type B | F 11 | – |
| *Clostridium botulinum* type C | 468 | – |
| *Clostridium botulinum* type D | 1873 | – |
| *Clostridium botulinum* type E | 9009 | – |
| *Clostridium botulinum* type F | NCIB 10658 | – |
| *Clostridium botulinum* type G | NCIB 10714 | – |
| *Clostridium barasii* (tox -) | ATCC 27639 | – |
| *Clostridium barasii* (tox F) | ATCC 43756 | – |
| *Clostridium butyricum* (tox -) | CB 25-1 | – |
| *Clostridium butyricum* (tox E) | ATCC 43181 | – |
| *Clostridium tetani* | E 19406 | – |
| *Clostridium sordellii* | IP 82 | – |
| *Clostridium bifermentans* | ATCC 638 | – |
| *Clostridium innoccuum* | NCIB 10674 | – |
| *Clostridium sporogenes* | ATCC 3584 | – |
| *Clostridium paraputrificum* | ATCC 25780 | – |
| *Clostridium difficile* | ATCC 9689 | – |
| *Clostridium difficile* | 203-1 | – |
| *Clostridium oedematiens* | ATCC 17861 | – |
| *Escherichia coli* O : 157 H7 | LCHA P1 | – |
| *Escherichia coli* O : 6 H16 | LCHA 877 | – |
| *Escherichia coli* O : 125 B15 | LCHA 483 | – |
| *Salmonella typhimurium* | 3612 | – |
| *Salmonella enteritidis* | 3625 | – |
| *Salmonella agona* | 3628 | – |
| Proteus sp | 720S | – |
| Kurthia sp | C4 | – |
| *Pseudomonas aeruginosa* | 32 | – |
| *Staphylococcus aureus* | C3-0 | – |
| *Yersinia enterocolitica* | S31 | – |

(1) Symbols used for PCR results:
–: Negative reaction for alpha-toxin and enterotoxin genes.
+: Positive reaction for alpha-toxin gene.
++: Positive reaction for alpha-toxin and enterotoxin genes.

TABLE 2

Stool samples investigation

| Samples | Number of sulfito-reductor bacteria | Duplex PCR | SLAT |
|---|---|---|---|
| 1 | $<10^4$ | – | – |
| 2 | $<10^4$ | – | – |
| 3 | $<10^4$ | – | – |
| 4 | $<10^4$ | + | – |
| 5 | $10^4$ | + | + |
| 6 | $10^4$ | + | + |
| 7 | $10^4$ | + | + |
| 8 | $2.10^4$ | + | + |
| 9 | $5.10^4$ | + | + |
| 10 | $5.10^4$ | + | + |
| 11 | $10^5$ | – | + |
| 12 | $10^5$ | + | + |
| 13 | $10^5$ | + | + |
| 14 | $2.10^5$ | – | – |
| 15 | $2.10^5$ | + | + |
| 16 | $8.10^5$ | + | + |
| 17 | $10^6$ | + | + |
| 18 | $2.10^6$ | + | + |
| 19 | $2.10^6$ | + | + |
| 20 | $10^7$ | + | + |
| 21 | $10^7$ | + | + |
| 22 | $10^7$ | + | + |
| 23 | $10^7$ | + | + |

TABLE 3

*C. perfringens* investigation in food samples

| | *C. perfringens* investigation in naturally contaminated food samples | | | *C. perfringens* investigation in artificially contaminated food samples | |
|---|---|---|---|---|---|
| Food sample | Total | Classical method | Duplex PCR | Total | Duplex PCR |
| Cooked food | 31 | 1 ($5 \times 10^5$) | 1 | 30 | 30 |
| Pork butchery | 13 | 1 ($10^3$) | 1 | 12 | 12 |
| Raw meat | 11 | 0 | 0 | 11 | 11 |
| Milk product | 2 | 0 | 0 | 2 | 2 |
| Salad | 2 | 0 | 0 | 2 | 2 |

What we claim is:

1. A primer selected from the group consisting of: SEQ ID NO:1, SEQ ID NO:2, SEQ ID NO:3, SEQ ID NO:4, and SEQ ID NO:5.

2. A primer selected from the group consisting of: SEQ ID NO:6, SEQ ID NO:7, and SEQ ID NO:8.

3. A process for the determination of the presence and the numeration of *C. perfringens* in a sample comprising the following steps:

isolating DNA from the sample, amplifying parts of the genes of *C. perfringens* encoding respectively the lecithinase and enterotoxin by chain polymerization with the specific primers of claims 1 and 2 to form amplification products, and detecting the amplification products to determine the presence and the numeration of *C. perfringens*.

4. A process according to claim 3 wherein the DNA is isolated from a food sample according to the following steps:

incubating the sample in a medium allowing the growth of *C. perfringens*, separating the bacteriae from the food particles by centrifugation, contacting the bacteriae with a resin for lysing them, and separating the DNA from bacterial fragments.

* * * * *

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
( A ) LENGTH: 24 base pairs
( B ) TYPE: Nucleic Acid
( C ) STRANDEDNESS: Single
( D ) TOPOLOGY: Linear ( i i ) MOLECULE TYPE: DNA (genomic)

( i i i ) HYPOTHETICAL: NO

-continued ( v i ) ORIGINAL SOURCE:
( A ) ORGANISM: Clostridium Perfringens ( x i ) SEQUENCE DESCRIPTION: SEQ ID NO: 1:

AAGTTACCTT TGCTGCATAA TCCC 24

( 2 ) INFORMATION FOR SEQ ID NO: 2:

( i ) SEQUENCE CHARACTERISTICS:
( A ) LENGTH: 24 base pairs
( B ) TYPE: Nucleic Acid
( C ) STRANDEDNESS: Single
( D ) TOPOLOGY: Linear ( i i ) MOLECULE TYPE: DNA (genomic)

( i i i ) HYPOTHETICAL: NO ( v i ) ORIGINAL SOURCE:
( A ) ORGANISM: Clostridium Perfringens ( x i ) SEQUENCE DESCRIPTION: SEQ ID NO: 2:

ATAGATACTC CATATCATCC TGCT 24

( 2 ) INFORMATION FOR SEQ ID NO: 3:

( i ) SEQUENCE CHARACTERISTICS:
( A ) LENGTH: 21 base pairs
( B ) TYPE: Nucleic Acid
( C ) STRANDEDNESS: Single
( D ) TOPOLOGY: Linear ( i i ) MOLECULE TYPE: DNA (genomic)

( i i i ) HYPOTHETICAL: NO ( v i ) ORIGINAL SOURCE:
( A ) ORGANISM: Clostridium Perfringens ( x i ) SEQUENCE DESCRIPTION: SEQ ID NO: 3:

TCAAAAGAAT ATGCAAGAGG T 21

( 2 ) INFORMATION FOR SEQ ID NO: 4:

( i ) SEQUENCE CHARACTERISTICS:
( A ) LENGTH: 24 base pairs
( B ) TYPE: Nucleic Acid
( C ) STRANDEDNESS: Single
( D ) TOPOLOGY: Linear ( i i ) MOLECULE TYPE: DNA (genomic)

( i i i ) HYPOTHETICAL: NO ( v i ) ORIGINAL SOURCE:
( A ) ORGANISM: Clostridium Perfringens ( x i ) SEQUENCE DESCRIPTION: SEQ ID NO: 4:

TTCTATCTTG GAGAGGCTAT GCAC 24

( 2 ) INFORMATION FOR SEQ ID NO: 5:

( i ) SEQUENCE CHARACTERISTICS:
( A ) LENGTH: 26 base pairs
( B ) TYPE: Nucleic Acid
( C ) STRANDEDNESS: Single
( D ) TOPOLOGY: Linear ( i i ) MOLECULE TYPE: DNA (genomic)

( i i i ) HYPOTHETICAL: NO

-continued ( v i ) ORIGINAL SOURCE:
( A ) ORGANISM: Clostridium Perfringens ( x i ) SEQUENCE DESCRIPTION: SEQ ID NO: 5:

GCTACTAGTT CTTTTACATT CTTTCC 26

( 2 ) INFORMATION FOR SEQ ID NO: 6:

( i ) SEQUENCE CHARACTERISTICS:
( A ) LENGTH: 29 base pairs
( B ) TYPE: Nucleic Acid
( C ) STRANDEDNESS: Single
( D ) TOPOLOGY: Linear ( i i ) MOLECULE TYPE: DNA (genomic)

( i i i ) HYPOTHETICAL: NO ( v i ) ORIGINAL SOURCE:
( A ) ORGANISM: Clostridium perfringens ( x i ) SEQUENCE DESCRIPTION: SEQ ID NO: 6:

GAAAGATCTG TATCTACAAC TGCTGGTCC 29

( 2 ) INFORMATION FOR SEQ ID NO: 7:

( i ) SEQUENCE CHARACTERISTICS:
( A ) LENGTH: 30 base pairs
( B ) TYPE: Nucleic Acid
( C ) STRANDEDNESS: Single
( D ) TOPOLOGY: Linear ( i i ) MOLECULE TYPE: DNA (genomic)

( i i i ) HYPOTHETICAL: NO ( v i ) ORIGINAL SOURCE:
( A ) ORGANISM: Clostridium Perfringens ( x i ) SEQUENCE DESCRIPTION: SEQ ID NO: 7:

GCTGGCTAAG ATTCTATATT TTTGTCCAGT 30

( 2 ) INFORMATION FOR SEQ ID NO: 8:

( i ) SEQUENCE CHARACTERISTICS:
( A ) LENGTH: 30 base pairs
( B ) TYPE: Nucleic Acid
( C ) STRANDEDNESS: Single
( D ) TOPOLOGY: Linear ( i i ) MOLECULE TYPE: DNA (genomic)

( i i i ) HYPOTHETICAL: NO ( v i ) ORIGINAL SOURCE:
( A ) ORGANISM: Clostridium Perfringens ( x i ) SEQUENCE DESCRIPTION: SEQ ID NO: 8:

GAACGCCAAT CATATAAATT TCCAGCTGGG 30